(12) United States Patent
Mafi et al.

(10) Patent No.: US 9,254,157 B2
(45) Date of Patent: Feb. 9, 2016

(54) BONE FRACTURE REDUCTION DEVICE AND METHODS USING SAME

(75) Inventors: Masourmeh Mafi, Mountain View, CA (US); Bryan Auyoung, Santa Clara, CA (US); Todd Jenkins, San Jose, CA (US); Warren Sapida, Sunnyvale, CA (US)

(73) Assignee: KYPHON SARL, Neuchatel (CH)

( * ) Notice: Subject to any disclaimer, the term of this patent is extended or adjusted under 35 U.S.C. 154(b) by 367 days.

(21) Appl. No.: 13/367,530

(22) Filed: Feb. 7, 2012

(65) Prior Publication Data

US 2013/0204268 A1 Aug. 8, 2013

(51) Int. Cl.
*A61B 17/58* (2006.01)
*A61B 17/60* (2006.01)
*A61F 2/00* (2006.01)
*A61B 17/88* (2006.01)
*A61B 19/00* (2006.01)

(52) U.S. Cl.
CPC ..... *A61B 17/8855* (2013.01); *A61B 2019/5466* (2013.01)

(58) Field of Classification Search
CPC ............ A61B 17/8855; A61B 17/025; A61B 2017/025; A61B 2017/0256; A61B 2019/5466
USPC ........................................ 606/90, 92–95, 105
See application file for complete search history.

(56) References Cited

U.S. PATENT DOCUMENTS

| | | | |
|---|---|---|---|
| 4,706,670 A * | 11/1987 | Andersen | A61L 29/06 604/526 |
| 6,663,647 B2 | 12/2003 | Reiley et al. | |
| 6,773,447 B2 * | 8/2004 | Laguna | A61M 25/1002 606/198 |
| 6,981,981 B2 | 1/2006 | Reiley et al. | |
| 2004/0225296 A1 * | 11/2004 | Reiss et al. | 606/90 |

* cited by examiner

*Primary Examiner* — David Bates
*Assistant Examiner* — Olivia C Chang
(74) *Attorney, Agent, or Firm* — Sorell Lenna & Schmidt LLP

(57) ABSTRACT

A device and method for treating bone fractures/lesions using an inflatable body is provided. The inflatable body includes a balloon having a substantially flat horizontal surface for quick easy insertion into bone beneath the fracture so as to align misaligned fragments of the fracture and/or to collapsed bone. The body has a shape and size to compress at least a portion of the cancellous bone to form a cavity in the cancellous bone and/or to restore the original position of the outer cortical bone, if fractured or collapsed. The inflatable body has a stylet attached to it's distal end so that once the inflatable body is deflated it can be twisted about the stylet to have a smaller profile so as to be easily withdrawn from the bone.

20 Claims, 7 Drawing Sheets

BONE FRACTURE REDUCTION DEVICE AND METHODS USING SAME

TECHNICAL FIELD

The present disclosure relates to inflatable devices for the treatment of bone fractures.

BACKGROUND

Fractures, lesion and collapsing of bone structure can occur in humans due to age, disease or trauma. There are many areas of bone that are prone to collapsing/depression, such as vertebra, proximal humerus, tibial plateau, distal radius and calcaneous. A bone tamp can be used to restore collapsed bone and re-align bone fragments caused by fractures followed by injection of bone cement to fill any fractures, as well as, the void created after the inflated device is removed. Precise positioning of the inflatable device beneath the deepest point of the depression in the collapsed area or bone fragments is essential in properly restoring the correct alignment of the bone fragments or reduction of the bone using a rounded inflatable device. If a round inflatable device is improperly placed beneath the depression, misalignment of the fragments or under/over reduction can result. Time and skill of the surgeon as well as limited work area to maneuver the device makes it difficult to always achieve proper placement. A better inflatable body that facilitates proper placement in bone is needed.

SUMMARY

This application is directed to a bone reduction device and method for treating fractures/lesions in bone. In particular, a bone reduction device is provided. The bone reduction device comprises a fill tube extending along a longitudinal axis having a proximal end, a distal end, and a lumen extending from the proximal end to the oppositely disposed distal end along the longitudinal axis. An inflatable body having a wall configured to define a fillable cavity is attached to the distal end of the fill tube and the fillable cavity is in fluid communication with the lumen of the fill tube. The inflatable body is configured to have a horizontal surface when inflated. The device also has a stylet positioned within the lumen of the fill tube and may or may not be attached to the distal end of the inflatable body. It is contemplated that the distal end of the fill tube, the distal end of the stylet or both can be attached so that when the fill tube and/or the stylet is twisted, the deflated inflatable body wraps around the fill tube so as to reduce it's profile for easy removal. The device further comprises an inner restraining member continuously connected to an inner surface of the wall of the inflatable body along the longitudinal axis so as to directionally restrain expansion of the inflatable body so as to define a substantially flat horizontal surface. The device is configured for insertion through a cannula into a bone adjacent a fracture so that it can be used to realign bone fragments misaligned due to a bone fracture and/or re-establishes height to a collapsed part of the bone.

In one embodiment, according to the principles of the disclosure, a method for treating fractures and collapsed bone is provided. The method uses a bone reduction device comprising a fill tube extending along a longitudinal axis having a proximal end, a distal end, and a lumen extending from the proximal end to the oppositely disposed distal end along the longitudinal axis. An inflatable body having a wall configured to define a fillable cavity attached to the distal end of the fill tube wherein the fillable cavity is in fluid communication with the lumen of the fill tube and a portion of the wall is made from a material having a higher durometer than the rest of the wall is provided. A portion of the inflatable body wall having a higher durometer reading causing it to inflate less than the rest of the inflatable body so as to form a substantially flat horizontal surface when inflated. The horizontal surface can be coated with radio-opaque or fluorescent material that is detectable by medical imaging devices so as to determine orientation of the horizontal surface when placed in the bone. This allows a user of the device, for example a surgeon, to make sure that the horizontal surface is properly positioned beneath the deepest point in the depression so that when inflated, the inflatable body provides an even and consistent pressure to the bone so as to result in proper repair of the collapsed area.

The device also has a stylet having first and second flattened portions, which is positioned within the lumen of the fill tube so that the distance between the first and second flattened portions define the length of the substantial flat horizontal surface. In one embodiment of the present disclosure, the stylet is attached to the distal end of the inflatable body so that when the stylet is rotated either in the clockwise or counter clockwise direction, the deflated inflatable body twists about the stylet so as to reduce the profile of the inflatable body for removal. Either the proximal and distal flattened portions of the stylet and/or the substantially flat horizontal surface is coated with a radio-opaque or fluorescent coating so as to indicate location and orientation of the flat surface. The device is configured for insertion through a cannula into the bone adjacent the fracture and/or beneath the collapsed bone.

A method for treating a bone fracture comprising preparing bone for receiving the device of the present disclosure is provided. Inserting the device into the bone wherein the inflatable body is in a deflated state. Once inserted, orientating the horizontal surface of the inflatable body below a fracture or collapsed portion of bone to be treated. Once oriented properly, inflating the inflatable body by adding fill material, for example saline or contrast, so that the horizontal surface compacts calcaneous bone and/or bone marrow to create a void and to aid in establishing zero malreduction of the bone. Once the proper reduction is established, the inflatable body is deflated and optionally twisted about the stylet located within the lumen and attached to the distal end so as to reduce the profile of the deflated inflatable body for easy removal from the bone. Removing the catheter from the bone.

BRIEF DESCRIPTION OF THE DRAWINGS

The present disclosure will become more readily apparent from the specific description accompanied by the following drawings, in which.

DETAILED DESCRIPTION

Figure 1:
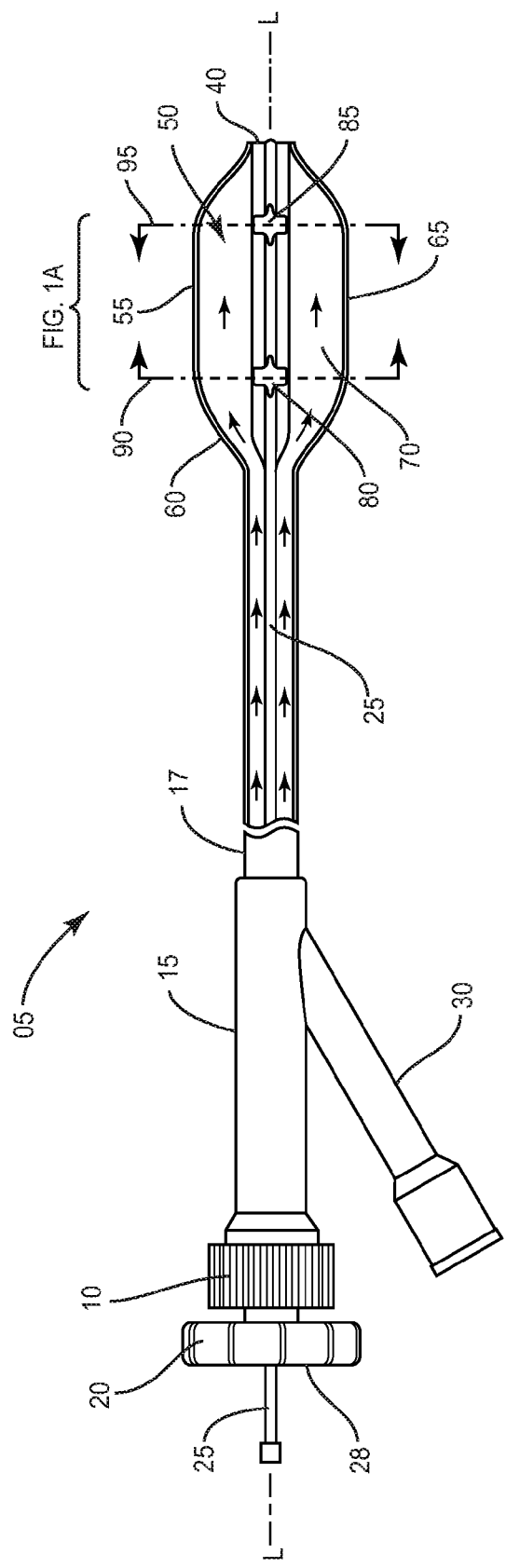
FIG. 1 is a perspective view of one particular embodiment of a bone fracture reduction device in accordance with the principles of the present disclosure.

A device and method is described for treating bone fractures and/or bone collapse. For illustrative purposes, the apparatus and method shall be described in the context of treating fractures and restoring proper reduction of a collapsed portion of a bone.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, distal and proximal, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament and/or bone, repairing a fracture or break in bone and other tissues; as an adjunct in surgery; and/or any repair procedure.

Also, as used in the specification and including the appended claims, the term "tissue" includes soft tissue, ligaments, tendons, cartilage and/or bone unless specifically referred to otherwise.

The term "reduction" as used in this application refers to a medical procedure to restore a fracture or dislocation to the correct alignment. When a bone fractures, the fragments lose their alignment in the form of displacement or angulation. For the fractured bone to heal without any deformity the bony fragments must be realigned to their normal anatomical position. Orthopedic surgeons attempt to recreate the normal anatomy of the fractured bone by reduction.

The following discussion includes a description of a device for treating bone lesions, fractures and/or collapsed bone and related methods of employing the device in accordance with the principles of the present disclosure. Alternate embodiments are also disclosed. Reference will now be made in detail to the exemplary embodiments of the present disclosure, which are illustrated in the accompanying figures. Turning now to FIGS. 1-12, there are illustrated components of the device for treating bone lesions, fractures and/or collapsed bone in accordance with the principles of the present disclosure.

The term "Touhy Borst" or "Y Tube" as used in the application refers to an adapter used for attaching catheters to various other devices.

The components of the bone reduction device can be fabricated from biologically acceptable materials suitable for medical apparatuses, including metals, synthetic polymers, ceramics, thermoplastic and polymeric material and/or their composites. For example, the components of the bone reduction device, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan, Fe—Mn—Si and Fe—Ni—Co—Ti composites), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, and composites of metals and calcium-based ceramics, composites of PEEK and calcium based ceramics, and combinations of the above materials. Various components of the anchoring bone reduction device may have material composites, including the above materials, to achieve various desired characteristics such as strength, rigidity, elasticity, compliance, and biomechanical performance, durability and to provide a non-stick surface. The components of the bone reduction device may be monolithically formed, extruded, coextruded, hot molded, cold molded, press molded, integrally connected or include fastening elements and/or coupling components, as described herein. In particular, the inflatable portion of the device according to the present disclosure can comprise flexible material, including (but not limited to) non-elastic materials such as PET, Mylar or Kevlar®, elastic materials such as polyurethane, latex or rubber, semi-elastic materials such as silicone, or other materials.

Since the inflatable body expands and comes in contact with cancellous bone, the materials used and thickness must have significant resistance so as to resist surface abrasion, puncture and/or tensile stresses. For example, structures incorporating elastomer materials, e.g., polyurethane, which have been preformed to a desired shape, e.g., by exposure to heat and pressure, can undergo controlled expansion and further distention in cancellous bone, without failure, while exhibiting resistance to surface abrasion and puncture when contacting cancellous bone. The present invention further discloses inflatable devices that have one or more biased directions of inflation. For example, inflatable devices having reduced lateral growth may provide improved fracture reduction because such devices can exert a greater vertical force and/or displacement within the treated bone. Such inflatable devices may also protect the lateral and anterior/posterior sidewalls of bone, for example long bone and vertebral body, by minimizing expansion towards these sidewalls and directing expansion to a greater degree along the longitudinal axis of the bone. In situations where a surgical procedure is terminated when the inflatable device contacts a lateral cortical wall of the targeted bone, such biased expansion could permit improved fracture reduction prior to reaching this procedure endpoint.

Figure 2:
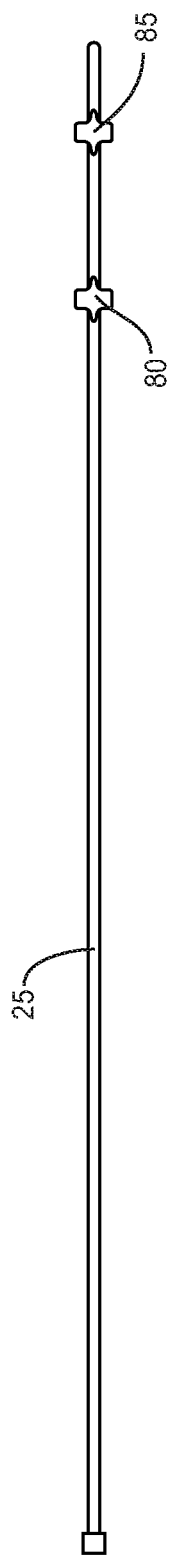
FIG. 2 a top view of a stylet as shown in FIGS. 1 and 1A constructed in accordance with the teachings of the present invention.
Figure 3:
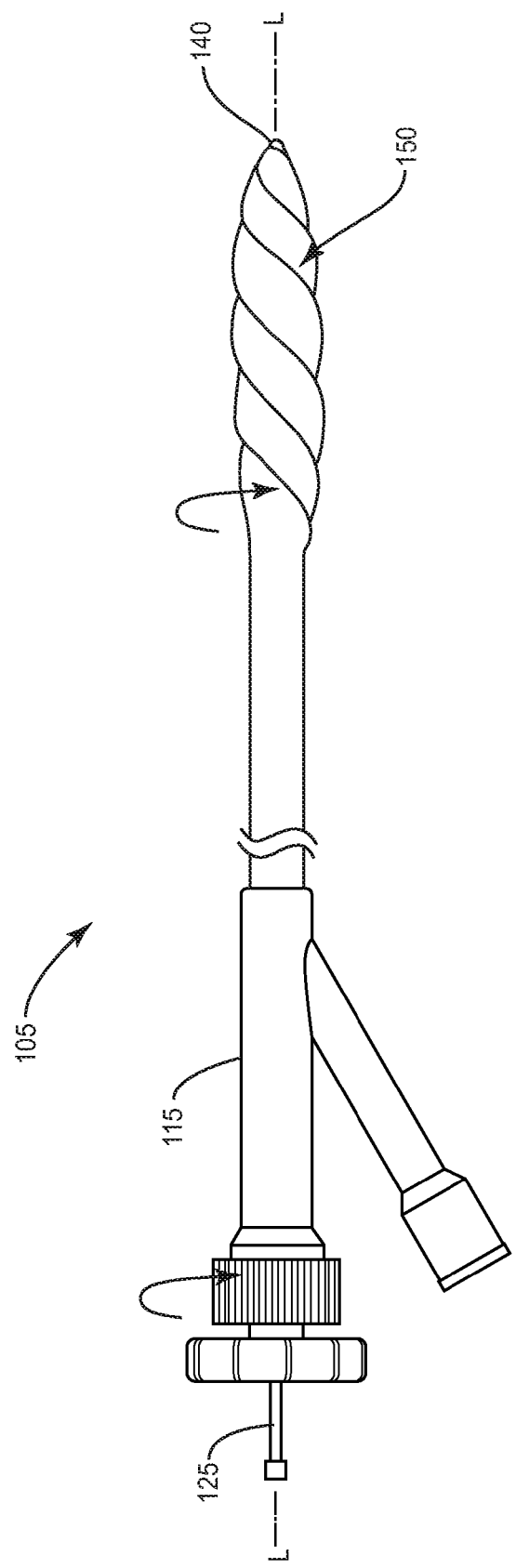
FIG. 3 is another perspective view of the bone fracture reduction device with the deflated inflatable body twisted about the distal end in accordance with the principles of the present disclosure of FIG. 1.

In one embodiment, as shown in FIGS. 1-3, the reduction device 05, in accordance with the present disclosure, comprises a body 15 having a longitudinal axis "L" attached to a fill tube 17. The fill tube 17 extends from body 15 to the distal end 40 of device 05. The device 05 includes a lumen extending from the proximal end 28 of body 15 to the oppositely disposed distal end 40 of device 05 along the longitudinal axis. This lumen extends through body 15, into fill tube 17 and is continuous with the fillable cavity 70 of inflatable body 50. The fillable cavity 70 is defined by wall 60 and is configured to inflate upon receiving fluid material from fill tube 17. That is, fillable cavity 70 is attached to the distal end of the fill tube 17 and is in fluid communication with the lumen of the fill tube 17 so that fluid material flowing from the fill tube 17 inflates inflatable body 50. The fluid material used to inflate inflatable body 50 can be in the form of a liquid or gas, for example, either saline or compressed air. When inflated, wall 60 of inflatable body 50 has a first wall portion 55 that defines a substantially flat horizontal surface that is configured to engage bone and provide force against bone fragments so as to realign the fragments. In one embodiment in accordance with the present disclosure, inflatable body 50 has a second wall portion 65 that defines a second substantially flat horizontal surface configured to engage bone, as does the first wall portion 55. A Y tube 30 is attached for attaching surgical devices as required by the procedure.

Figure 1A:
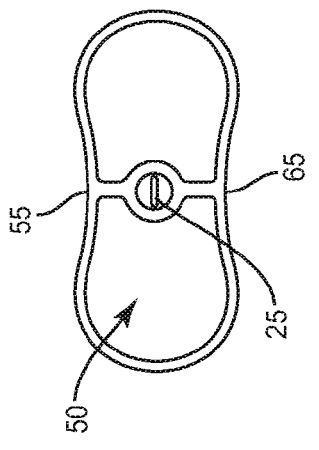
FIG. 1A is a cross section between the arrows indicated in FIG. 1.

FIG. 1A is a cross-section of the inflatable body 50 showing the flat stylet 25 at the dotted lines 90 and 95 shown in FIG. 1. In one embodiment of the present disclosure, stylet 25 has a predominately round configuration with two flattened portions 80, 85 spaced apart from one as shown in FIG. 1. Flat marker portions 80 and 85 are specifically positioned on stylet 25, as shown in FIG. 2, so as to correspond to the proximal and distal boundaries of the substantially flat surfaces 55 and 65 of the inflatable body. Flat marker portions 80 and 85 can be used to replace gold and/or platinum marker bands often used as markers that not only add greatly to the cost of the stylet but also require additional manufacturing steps to adhere the markers to the stylet 25. In addition, the gold/platinum markers can shift and therefore lead to imprecise readings. Relying on imprecise readings can result in placement of the substantially flat surfaces 55 and 65 in a position that results in misalignment or malreduction when inflated.

The flat marker surfaces 80 and 85 can be produced in the stylet 25 so that the flat surface of the marker is parallel with substantially flat surfaces 55 and 65 thereby providing not only boundaries for the substantially flat surfaces 55 and 65 but also provide information for proper orientation of inflatable body 50. Therefore, locating flat marker surfaces 80 and 85 using a medical imaging or fluoroscope when device 05 is inserted into bone allows the surgeon to determine not only the positioning of the substantially flat surfaces 55 and 65 but also the orientation of these surfaces. This information allows for precise placement of the inflatable body 50, which often leads to better fracture repair.

Stylet 25 can have different shapes, such as, for example, round, oval, oblong, square, rectangular, polygonal, irregular, uniform, non-uniform, offset, staggered, tapered, consistent or variable, depending on the requirements of a particular application. In one embodiment in accordance with the present disclosure, stylet 25 is round, for example a stainless steel wire, and is configured to have a proximal flattened portion 80 and a distal flattened portion 85. As shown in FIG. 1, proximal flattened portion 80 and a distal flattened portion 85 of stylet 25 is positioned so as to define the proximal end of substantially flat horizontal surfaces 55, 65 and the distal end of substantially flat horizontal surfaces 55, 65. That is, the position of portions 80 and 85 defines the length and location of the proximal and distal ends of the substantially flat horizontal surfaces 55, 65, for example the distance between 90 and 95 in FIG. 1. These flattened portions 80 and 85 of stylet 25 can be marked, for example with a radio-opaque enhancer or fluorescent coating, so that detecting these markers indicates the position, location and length of substantially flat horizontal surfaces 55, 65, so as to aid in the placement of the inflatable body 50 to assure proper alignment of fracture fragments reduction of collapsed bone.

As stated above, flattened portions 80 and 85 of stylet 25 eliminates the need for expensive platinum or gold markers/bands designed to mark the beginning and end of the substantially flat surface and provide information about the orientation of the horizontal surfaces 55, 65. This makes device 05 more economical to make and use. Stylet 25 of the present disclosure is easily and inexpensively manufactured by crimping a stainless steel wire, to produce a round stylet having flattened proximal and distal portions. Other materials and shapes for the stylet are also contemplated. Once flattened portions 80, 85 are produced, they can be coated with radio-opaque or fluoresce material for identification during placement.

FIG. 3 shows device 105 having stylet 125 extending through the lumen of body 115 to distal end 140. At distal end 140 stylet 125 is attached to the distal end of the inflatable body 150 so that rotation of stylet 125 in a clockwise or counter clockwise twists inflatable body 150 about stylet 125 so as to reduce its profile for existing out of bone.

Figure 4:
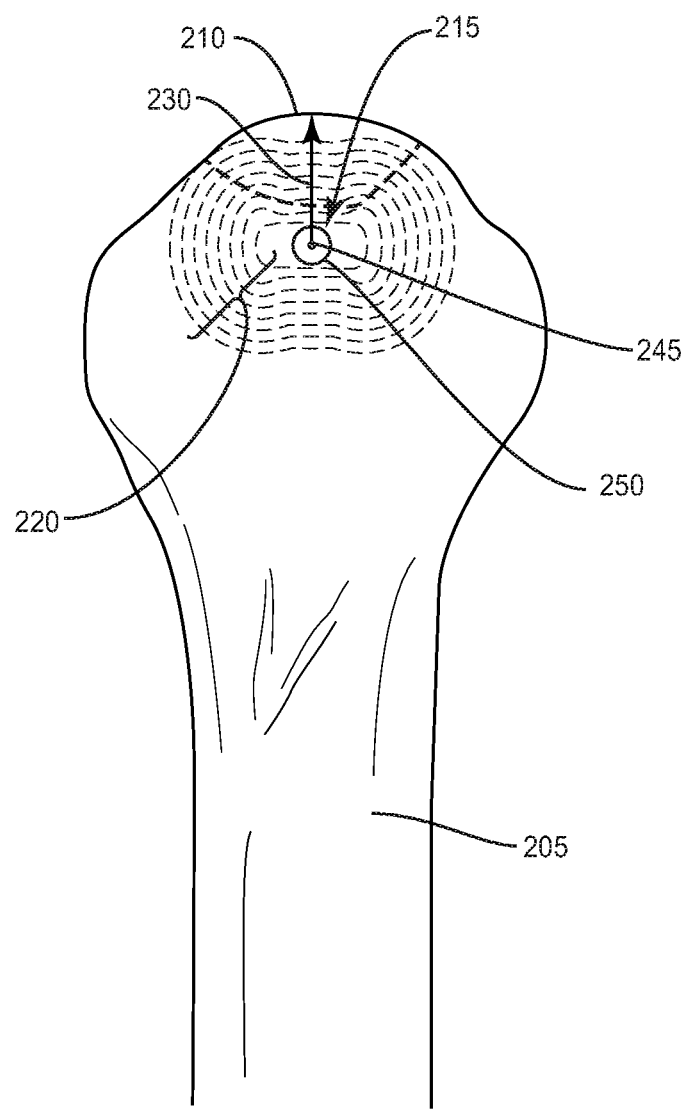
FIG. 4 is a perspective view of the bone fracture reduction device for use in a long bone such as the tibial plateau, constructed in accordance with the teachings of the present invention.

FIG. 4 shows the device in operation in a long bone. An inflatable body 250 having a substantially flat horizontal surface and stylet 245 is inflated in accordance with the present disclosure. As shown, the distal end 210 of long bone 205 is collapsed with the deepest point 215 having fractures therein. The substantially flat horizontal surface of inflatable body 250 is positioned beneath the deepest depression point 215. As the inflatable body 250 is inflated in accordance with the present disclosure, it expands along path 220 so as to engage and apply force to the deepest point 215 and surrounding area. As it is inflated, the substantially flat horizontal surface of inflatable body 250 pushes against the bone applying constant and equal pressure so as to reestablish the height of the collapsed bone along path 230. Expansion of the inflatable body

250 also aligns fragments of bone caused as result of the fracture so as to facilitate proper healing of the fractured bone.

Figure 5:
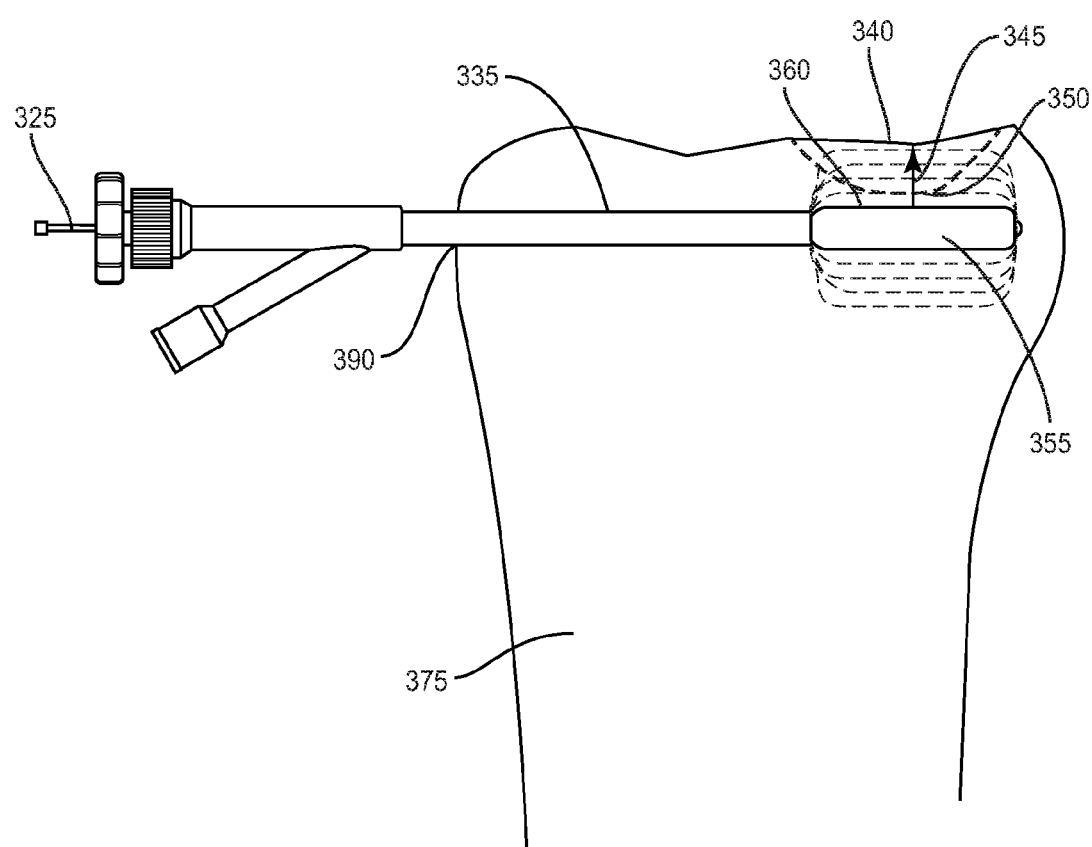
FIG. 5 is an anterior/posterior view of the bone fracture reduction device for use in a long bone such as the tibial plateau, constructed in accordance with the teachings of the present invention of FIG. 4.

FIG. 5 shows the anterior/posterior view of the device 335 inserted into bone at point 390 in operation similar to FIG. 4. As with the embodiment shown in FIG. 4, an inflatable body 355 having a substantially flat horizontal surface 360 is positioned directly beneath the deepest depression point 350 and is inflated in accordance with the present disclosure. In accordance with the teachings of the present disclosure, stylet 325 having flat portions (not shown) is used to properly position the substantially flat horizontal surface 360 beneath the deepest depression point 350 of the collapsed bone so that when inflated, the inflatable body displaces along path 345 and presses against the deepest depression point 350 of the bone applying constant and equal pressure so as to reestablish the height of the collapsed bone. Expansion of the inflatable body 355 aligns fragments of bone caused as result of the fracture so as to facilitate proper healing of the fractured bone.

In realigning bone fragments of a fracture and/or re-establishing height to a collapsed bone, proper placement of the inflatable body 355 is essential. That is, to realign and correct collapsed bone, placing the substantially flat portion of the inflatable body 355 properly beneath the fracture or collapsed area is essential for a favorable outcome of the treatment. The substantially flat horizontal surface of the device allows for easy placement under the fracture and/or collapsed area of the bone so that upon inflation of the fragments are realigned and/or collapsed bone is corrected. In contrast, round or spherical shaped balloons are more difficult to properly place in situ due to the curvature of the balloon. If not positioned below the deepest point of the depression, once expanded the round portion of the inflatable body only partially restores the height of the collapsed bone. That is, the point directly under the outermost point of the round balloon is advance higher than the rest of the balloon therefore leading to incomplete correction of collapsed bone and/or misalignment of the bone fragments. Thus, the inflatable body of the present disclosure, having flat surfaces parallel to the flat portions of the stylet, allows for proper placement of the inflatable body prior to expansion. Proper placement is essential in treating fractures and collapsed bones, for example in extremities of a human. Accordingly, a stylet having flattened portions that define the boundaries of the substantially flat surfaces as well as the orientation of the surfaces allows a surgeon to place the inflatable body properly in situ therefore making it easier and less time consuming to achieve proper placement of the inflatable body prior to inflation. This ultimately leads to a better outcome and less time in surgery for a patient.

Figure 6:
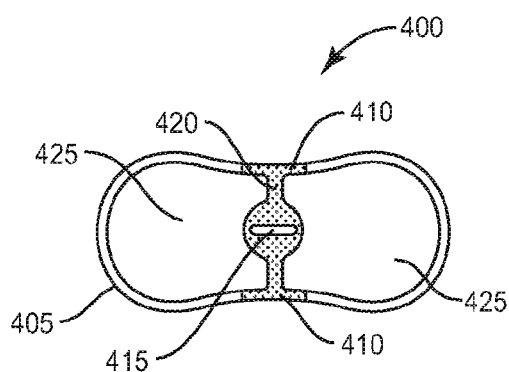
FIG. 6-FIG. 12 are cross sectional views of various shapes of the inflatable body of the bone fracture reduction device in accordance with the teachings of the present invention; and Like reference numerals indicate similar parts throughout the figures.

FIG. 5-FIG. 12 show different configurations of the inflatable body in accordance with the features and operations of the present disclosure. FIG. 6 is a cross section across the inflatable body 400 of the present disclosure at the flattened portion of the stylet 415. The outer wall of the inflatable body 400 includes a wall having a first portion 410 made of material having a higher durometer, therefore less elastic than a second portion 405 having a lower durometer. The second portion 405 of the wall having a lower durometer reading than the first portion 410. The wall can extend into the fillable cavity 425 along a longitudinal axis of the wall and attached to an inner surface of the wall, like a bridge, beneath the substantially flat horizontal surface of the inflatable body. This bridge section 420 extends from one side of the inflatable body to the other and prevents the inflatable body from fully expanding so as to establish the substantially flat horizontal surface of the inflatable body. This section can be made form material having a higher durometer than the rest of the wall and therefore will not expand as much as the wall section having a lower durometer so as to produce the configuration shown in FIG. 6. The outer surface of first portion 410 can contain ink, radio-opaque markings or fluorescence materials so that this section can be tracked when positioning the inflatable body in situ.

Figure 7:
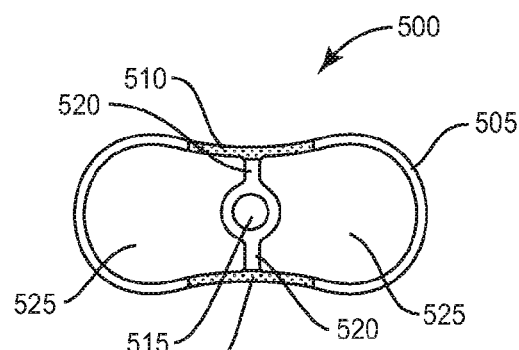

FIG. 7 is a cross section across the inflatable body 500 of the present disclosure at the flattened portion of the stylet 515. The outer wall of the inflatable body 500 includes a wall having a first portion 510 made of material having a higher durometer than a second portion 505. The second portion 505 of the wall having a lower durometer reading than the first portion 510. The wall can extend into the fillable cavity 525 along a longitudinal axis of the wall and attached to an inner surface of the wall, like a bridge 520, beneath the substantially flat horizontal surface of the inflatable body. This bridge section 520 extends from one side of the inflatable body to the other and prevents the inflatable body from fully expanding so as to establish the substantially flat horizontal surface of the inflatable body. This section can be made form material having a lower durometer than the rest of the wall and therefore will expand more than the wall section having a higher durometer so as to produce the configuration shown in FIG. 7. The outer surface of first portion 510 can contain ink, radio-opaque markings or fluorescence materials so that this section can be tracked when positioning the inflatable body in situ.

Figure 8:
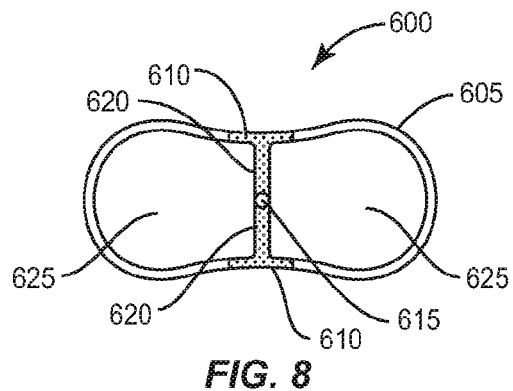

Similar to FIG. 6, FIG. 8 is a cross section across the inflatable body 600 of the present disclosure at the flattened portion of the stylet 615. The outer wall of the inflatable body 600 includes a wall having a first portion 610 having a higher durometer, therefore less elastic than a second portion 605 having a lower durometer. The second portion 605 of the wall having a lower durometer reading than the first portion 610. The wall can extend into the fillable cavity 625 along a longitudinal axis of the wall and attached to an inner surface of the wall, like a bridge 620, beneath the substantially flat horizontal surface of the inflatable body. This bridge section 620 extends from one side of the inflatable body to the other and prevents the inflatable body from fully expanding so as to establish the substantially flat horizontal surface of the inflatable body. Unlike the bridge section 420 in FIG. 6, the bridge 620 in FIG. 8, has a straight configuration wherein the bridge section 420 in FIG. 6 bulges outwardly around stylet 415. This section is made from material having a higher durometer than the rest of the wall and therefore will expand less than the wall section having a lower durometer so as to produce the configuration shown in FIG. 8.

Figure 9:
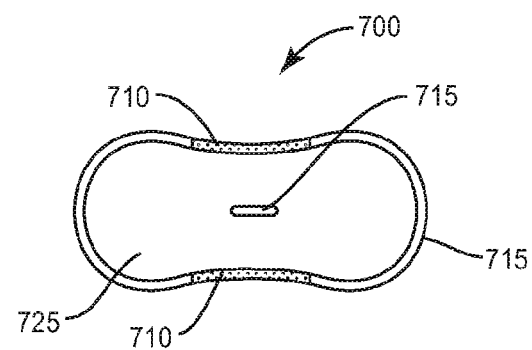

FIG. 9 is a cross section across the inflatable body 700 of the present disclosure at the flattened portion of the stylet 715. The outer wall of the inflatable body 700 includes a wall having a first portion 710 made of material having a higher durometer than a second portion 705. The second portion 705 of the wall having a lower durometer reading than the first portion 710. Unlike FIGS. 6-8, the inflatable member of FIG. 9 has no bridge section and the stylet is disposed in the internal cavity 725 to produce the configuration shown in FIG. 9.

Figure 10:
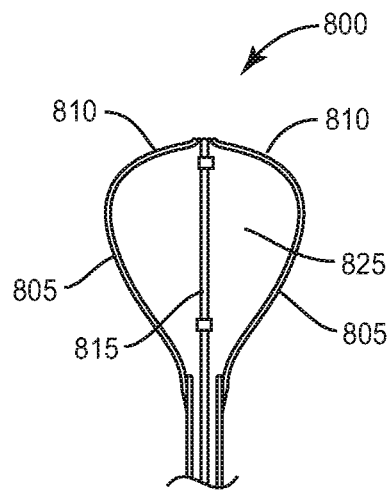

FIG. 10 is a longitudinal cross section across the inflatable body 800 of the present disclosure along the portion of the stylet 815. The outer wall of the inflatable body 800 formed from a wall having a first portion 810 made of material having a higher durometer, therefore less elastic than a second portion 805. The second portion 805 of the wall having a lower durometer reading than the first portion 810. Unlike FIGS. 6-9, the inflatable member 800 of FIG. 10 has no bridge section and stylet 815 is disposed in the internal cavity 825 to produce a triangular, parachute shaped configuration as shown in FIG. 10. The tip of stylet 815 being attached to the distal end of the inflatable body 800.

Figure 11:
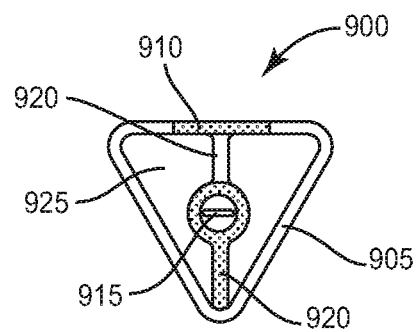

Similar to FIG. 10, FIG. 11 has a triangular shape. FIG. 11 shows a cross section across the inflatable body 900 of the present disclosure at the flattened portion of the stylet 915. The outer wall of the inflatable body 900 formed from a wall having a first portion 910 having a higher durometer, therefore less elastic, than a second portion 905 having a lower durometer. The second portion 905 of the wall having a lower durometer reading than the first portion 910. The wall can extend into the fillable cavity 925 along a longitudinal axis of the wall and attached to an inner surface of the wall, like a bridge 920, beneath the substantially flat horizontal surface of the inflatable body. This bridge section 920 extends from one side of the inflatable body to the other and prevents the inflatable body from fully expanding so as to establish the substantially flat horizontal surface of the inflatable body. Unlike the bridge section in FIGS. 6-9, bridge 920, has a portion that has a higher durometer and a section having a lower durometer. The lower durometer section can be positioned below the first section of the wall 910 wherein the higher durometer of the bridge is positioned at an apex of the triangular/wedged shaped inflatable body. The section made from material having a higher durometer will expand less than the rest of the wall so as to produce the wedge shape configuration shown in FIG. 11.

Figure 12:
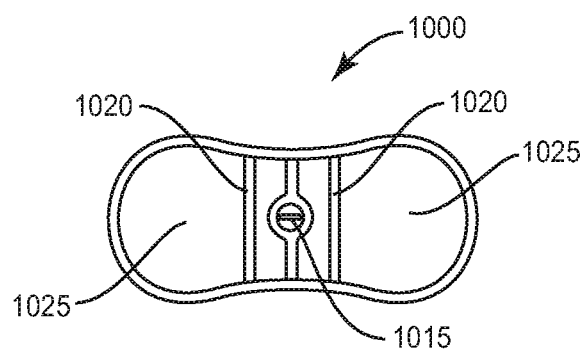

Similar to FIGS. 6-8, FIG. 12 is a cross section across the inflatable body 1000 of the present disclosure at the flattened portion of the stylet 1015. The outer wall of the inflatable body 1000 formed from a wall having a uniform durometer. The wall can extend into the fillable cavity 1025, or have attached to the inside surface of the wall one or more restraining bridges 1020 that extend along a longitudinal axis of the wall beneath the substantially flat horizontal surface of the inflatable body. These bridge sections 1020 extend from one side of the inflatable body 1000 to the other and prevent the inflatable body from fully expanding so as to establish the substantially flat horizontal surface of the inflatable body. These bridge sections 1020 can be made from material having the same of different durometer reading or can be the same or different thickness so as to produce the configuration shown in FIG. 12. The proximal end of the inflatable body in FIG. 12 is attached to a catheter so that it can be filled with filling material as described herein.

As discussed above, spherical portions of the inflatable body may be restrained by using inelastic, semi-elastic, elastic and elastomeric materials in the construction of the inflatable body, or may be additionally restrained as described. The material of the inflatable body can be a non-elastic material, such as polyethylene tetraphthalate (PET), nylon, Kevlar® or other medical inflatable body/balloon materials. It can also be made of semi-elastic materials, such as silicone, rubber, thermoplastic rubbers and elastomers or elastic materials such as latex or polyurethane, if appropriate restraints are incorporated. The restraints can be continuous or made of discrete elements of a flexible, inelastic high tensile strength material having the same or different durometer and thicknesses. The thickness of the inflatable body is typically in the range of $2/1000$ths to $25/1000$ths of an inch, although other thicknesses that can withstand increased pressures, such as 250-400 psi or greater, even up to 500, 1000 or 2000 psi, may be used.

Since the inflatable body expands and comes in contact with cancellous bone, the materials used and thickness of the wall of the inflatable body must have significant resistance so as to resist surface abrasion, puncture and/or tensile stresses. For example, structures incorporating elastomer materials, e.g., polyurethane, which have been preformed to a desired shape, e.g., by exposure to heat and pressure, can undergo controlled expansion and further distention in cancellous bone, without failure, while exhibiting resistance to surface abrasion and puncture when contacting cancellous bone. The present invention further discloses inflatable devices that have one or more biased directions of inflation. For example, inflatable devices having reduced lateral growth may provide improved fracture reduction because such devices can exert a greater vertical force and/or displacement within the treated bone. Such inflatable devices may also protect the lateral and anterior/posterior sidewalls of the vertebral body by minimizing expansion towards these sidewalls and directing expansion to a greater degree along the longitudinal axis of the spine. In situations where a surgical procedure is terminated when the inflatable device contacts a lateral cortical wall of the targeted bone, such biased expansion could permit improved fracture reduction prior to reaching this procedure endpoint.

The present invention further discloses inflatable devices having biased inflation along the longitudinal axis of the inflatable devices. Inflatable devices capable of biased inflation along their longitudinal axes may provide improved fracture reduction as such devices can be preferentially expanded towards areas of higher cancellous bone density and/or away from areas of lower cancellous bone density. Similarly, inflatable devices capable of biased inflation along their longitudinal axes can be preferentially expanded towards areas that resist expansion of the device and/or away from areas that promote expansion of the device.

Due to the nature of the injury, disease or other treatments, as well as the health and age of the patient suffering from these injuries, it may be preferable to treat a bone with the devices of this disclosure during an open or semi-open surgical procedure. In addition, a goal of the surgery may be to replace the diseased or injured bone with materials (such as bone fillers or certain drugs) which do not flow, and which thus are not well suited for a more minimally invasive procedure.

In assembly and use, the bone reduction device described herein is employed with a surgical procedure for treatment of a disorder affecting a section of bone, such as a fracture, for example in a vertebrae or extremity of a patient. In use, the bone reduction device wherein the inflatable body is initially deflated and, after the bone to be filled with the inflatable body has been prepared to receive the inflatable body (such as by punching, drilling or otherwise displacing a small amount of the cancellous bone directly beyond the opening of the cannula), is advanced into the bone through a cannula. The inflatable device is oriented preferably in the bone such that the substantially flat horizontal surface is positioned beneath the fracture, using the flattened portions of the stylet and fluoroscope/medical imaging material to effect orientation and placement in accordance with the description of the present disclosure. Once in place, filler material is directed into the fillable cavity of the expandable cavity so as to expand the inflatable cavity and exert pressure on the cortical bone to realign fragments of the fracture and/or elevate collapsed bone to its proper height. (FIGS. 4-5). Where such fracture or collapse has not occurred, such pressure would desirably compress the bone marrow and/or cancellous bone against the inner wall of the cortical bone, thereby compacting the bone marrow of the bone to be treated and to further enlarge the cavity in which the bone marrow is to be replaced by a biocompatible, flowable bone material, such as bone void filler/bone cement.

The inflatable body is inflated to compact the bone marrow and/or cancellous bone in the cavity and, after compaction of the bone marrow and/or cancellous bone, the inflatable body is deflated and removed from the cavity. Following compaction of the bone marrow, the inflatable body is deflated and the stylet twisted so as to coil the inflatable body about the stylet and reduce the profile of the inflatable body prior to removal. The lower profile makes it easier for the device to be pulled out of the cavity by applying a manual pulling force to the catheter tube.

It should be understood that the various embodiments of inflatable body disclosed herein are by no means limited in their utility to use in a single treatment location within the body. Rather, while exemplary treatment location, these embodiments can be utilized in various locations within the human body are provided; this disclosure should not be so limited. For example, the device according to the present disclosure can be useful in treating a fractures in various other areas within the body, including but not limited to fractures and/or impending fractures of the femur, the radius, the ulna, the tibia, the humerus, or the spine. Similarly, the various other disclosed embodiments can be utilized throughout the body, with varying results depending upon treatment goals and/or the anatomy of the targeted bone.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone reduction device comprising:
a fill tube extending along a longitudinal axis from a proximal end to an opposite distal end, the fill tube comprising an inner surface that defines a lumen extending from the proximal end to the distal end along the longitudinal axis;
an inflatable body attached to the distal end of the fill tube, the inflatable body having an inner surface that defines a fillable cavity, the fillable cavity being in fluid communication with the lumen;
an inner restraining member continuously connected to the inner surface of the inflatable body along the longitudinal axis so as to restrain expansion of the inflatable body in a manner that defines a flat horizontal exterior surface of the inflatable body when the inflatable body is fully inflated; and
a stylet positioned within the lumen, the stylet comprising proximal and distal flat marker portions, the flat horizontal exterior surface extending along the longitudinal axis from the proximal flat marker portion to the distal flat marker portion.

2. A bone reduction device comprising:
a fill tube extending along a longitudinal axis having a proximal end, a distal end, and a lumen extending from the proximal end to the oppositely disposed distal end along the longitudinal axis;
an inflatable body having a wall configured to define a fillable cavity attached to the distal end of the fill tube wherein the fillable cavity is in fluid communication with the lumen of the fill tube and the inflatable body is configured to have a flat horizontal exterior surface when inflated;
an inner restraining member continuously connected to an inner surface of the wall of the inflatable body along the longitudinal axis so as to restrain expansion of the inflatable body so as to define the flat horizontal exterior surface; and
a stylet positioned within the lumen of the fill tube and comprising proximal and distal flat marker portions;
wherein the device is configured for insertion through a cannula into a bone adjacent a fracture and the flat horizontal exterior surface extends in a longitudinal direction from the proximal flat marker portion to the distal flat marker portion of the stylet.

3. A bone reduction device according to claim 2 wherein the proximal and distal flat marker portions of the stylet are coated with radio-opaque material.

4. A bone reduction device according to claim 2 wherein the wall of the inflatable body has a first wall portion comprising material having a low durometer and a second wall portion comprising material having a higher durometer than the first wall portion wherein when the inflatable body is inflated it produces the flat horizontal exterior surface that is configured to engage bone and apply force against the bone when inflated.

5. A bone reduction device according to claim 2 wherein the wall of the inflatable body comprises a first wall portion having a thickness that is thicker than a thickness of a second wall portion wherein when the inflatable body is inflated it produces the flat horizontal exterior surface that is configured to engage bone and apply force against the bone when inflated.

6. A bone reduction device according to claim 2 further comprising a radio-opaque coating applied to a portion of the horizontal exterior surface of the wall of the inflatable body so that the orientation of the flat horizontal exterior surface inside a surgical site can be determined.

7. A bone reduction device according to claim 2 wherein the stylet is flat and is coated with radio-opaque material so that the orientation of the flat horizontal exterior surface inside a surgical site can be determined.

8. A bone reduction device according to claim 2 wherein at least a part of the wall of the inflatable body defining the at least one horizontal exterior surface comprises an internal device which restrains the wall from expanding beyond the flat horizontal exterior surface.

9. A bone reduction device according to claim 8 wherein the material of the internal restraint is selected from the group consisting of fibrous material, woven material, polymeric material, non-elastic material, and combinations thereof.

10. A bone reduction device according to claim 2 wherein the inflatable body comprises a balloon.

11. A bone reduction device according to claim 10 wherein the balloon is unidirectional, omnidirectional and/or multiple lumen.

12. A bone reduction device according to claim 2 wherein a first transverse axis extends through the proximal flat marker portion and a second transverse axis extends through the distal flat marker portion, the transverse axes extending perpendicular to the longitudinal axis, the inflatable body tapering proximal of the first transverse axis and distal of the second transverse axis.

13. A bone reduction device according to claim 2 wherein the inflatable body is configured to have the flat horizontal exterior surface when the inflatable body is fully inflated.

14. A bone reduction device comprising:
a catheter having a lumen along a longitudinal axis; and
a bone reduction device comprising:
a fill tube positioned within the catheter extending along a longitudinal axis, the fill tube having a proximal end, a distal end, and a lumen extending from the proximal end to the oppositely disposed distal end along the longitudinal axis;

an inflatable body having a wall configured to define a fillable cavity attached to the distal end of the fill tube wherein the fillable cavity is in fluid communication with the lumen of the file tube, the inflatable body having a first wall portion comprising material having a low durometer and a second wall portion comprising material having a higher durometer than the first wall portion so as to produce a flat horizontal exterior surface configured to engage bone and apply force against the bone when inflated;

a stylet positioned within the lumen of the fill tube and attached to the distal end of the inflatable body, the stylet having a radio-opaque proximal flat portion spaced apart along the longitudinal axis from a radio-opaque distal flat portion, the flat horizontal exterior surface extending in a longitudinal direction from the proximal flat portion to the distal flat portion; and an inner restraining member continuously connected to an inner surface of the wall of the inflatable body along the longitudinal axis so as to restrain expansion of the inflatable body so as to define the flat horizontal exterior surface.

15. A bone reduction system according to claim 14 wherein the flat horizontal exterior surface is coated with a radio-opaque material.

16. A bone reduction system according to claim 14 wherein the inflatable body comprises a balloon.

17. A bone reduction system according to claim 14 wherein the inner restraining member has a higher durometer than the rest of the wall of the inflatable body.

18. A bone reduction system according to claim 14 having at least one additional flat horizontal exterior surface.

19. A bone reduction system according to claim 14 wherein at least a portion of the wall of the horizontal surface has a higher durometer than the rest of the wall so as to aid in producing the flat horizontal exterior surface.

20. A bone reduction system according to claim 14 wherein a first transverse axis extends through the proximal flat marker portion and a second transverse axis extends through the distal flat marker portion, the transverse axes extending perpendicular to the longitudinal axis, the inflatable body tapering proximal of the first transverse axis and distal of the second transverse axis.

* * * * *